United States Patent
Wright

(12) 
(10) Patent No.: US 6,419,902 B1
(45) Date of Patent: Jul. 16, 2002

(54) COLOR CHANGING TOOTHPASTE

(76) Inventor: Howard W. Wright, 9772 Fall Ridge Trail, Sunset Hills, MO (US) 63127

(*) Notice: Subject to any disclaimer, the term of this patent is extended or adjusted under 35 U.S.C. 154(b) by 0 days.

(21) Appl. No.: 08/902,248

(22) Filed: Jul. 29, 1997

Related U.S. Application Data

(63) Continuation of application No. 08/570,315, filed on Dec. 11, 1995, now abandoned.

(51) Int. Cl.⁷ ................................................. A61K 7/16
(52) U.S. Cl. ............................ 424/49; 424/50; 424/51; 424/52; 424/53; 424/54; 424/55; 424/56; 424/57; 424/58
(58) Field of Search ...................... 424/49–58

(56) References Cited

U.S. PATENT DOCUMENTS

| | | | | |
|---|---|---|---|---|
| 2,789,731 A | * | 4/1957 | Marraffino | 222/129 |
| 3,747,232 A | * | 7/1973 | Donaldson et al. | 35/26 |
| 3,747,804 A | * | 7/1973 | Raaf et al. | 221/1 |
| 4,428,929 A | * | 1/1984 | Wicheta et al. | 424/49 |
| 4,456,585 A | * | 6/1984 | Hayes et al. | 424/49 |
| 4,487,757 A | * | 12/1984 | Kiozpeoplov | 424/44 |
| 4,715,518 A | * | 12/1987 | Moore | 222/257 |
| 4,830,221 A | * | 5/1989 | Mazzanobile | 222/92 |
| 4,969,767 A | * | 11/1990 | Madden | 401/261 |
| 5,009,881 A | * | 4/1991 | Hill et al. | 424/49 |
| 5,145,667 A | * | 9/1992 | Ibrahim et al. | 424/52 |
| 5,324,505 A | * | 6/1994 | Kornettka et al. | 424/49 |
| 5,553,747 A | * | 9/1996 | Raba et al. | 222/94 |
| 5,590,818 A | * | 1/1997 | Raba et al. | 222/575 |
| 5,683,679 A | * | 11/1997 | Sharma | 424/53 |

OTHER PUBLICATIONS

"Aquafresh" Tripe Protection Toothpaste With Triple Stripe Logo any Questions? Call Toll–Free 1 800 897 5623 Weekdays, 1999.*
"Aquafresh" Registered Trademark 1 765 467 First Used in Commerce May 1991 "Triple Stripe" (Red, White, & Green), Apr. 20, 1993.*
"Aquafresh" Registered Trademark 2 147 220 First Used in Commerce Jan. 1985 "Triple Stripe" Logo: Red Green Bluish Green and Blue, Mar. 31, 1998.*
"Aqufresh" Registered Trademark 1951495 First Used in Commerce Dec. 12, 1994 "Triple Stripe", Jan. 23, 1996.*
"Aquafresh" Registered Trademark 1908065 First Used in Commerce May 1991 Triple Stripe Red White Green, Blue, Aug. 1, 1995.*

* cited by examiner

*Primary Examiner*—Marianne C. Seidel
(74) *Attorney, Agent, or Firm*—Senniger, Powers, Leavitt & Roedel

(57) ABSTRACT

Disclosed is a color changing toothpaste which contains color reagents for interacting to provide a color change indicative of tooth brushing time. The color reagents comprise two separate color components which may be an FD&C dye, and FD&C lake or a natural food color, the two separate color components being adapted to interact after a predetermined brushing time to produce a third color. Optionally, the toothpaste may contain up to approximately 0.05% by weight of a foaming agent and other components such as a fluoride and a flavoring agent or flavor burst component.

18 Claims, No Drawings

COLOR CHANGING TOOTHPASTE

This is a continuation, of application Ser. No. 08/570,315, filed Dec. 11, 1995, now abandoned.

BACKGROUND OF THE INVENTION

This invention relates to toothpaste or dentrifice compositions and, more particularly, to such compositions which are formulated to provide a color change after a predetermined brushing time which renders the compositions especially suitable for use by children.

As is known, inducing children (and adults to some extent) to brush their teeth on a regular basis presents a difficult challenge. The brushing of teeth is perceived as a bothersome necessity by many adults and even more so by children. Insofar as children are concerned, the problem is exacerbated by the fact that children are highly sensitive to bitter tastes, possess a heightened gag reflex and typically utilize an equal amount of toothpaste as adults while having a mouth that is one fourth the size of the adult mouth. Thus, not only is brushing of the teeth an uncomfortable experience for children, but additionally a child's lack of appreciation of the benefits of regular brushing coupled with a child's short attention span renders the twice daily brushing regimen devoid of any positive reinforcement for the typical child.

The availability of a toothpaste or dentrifice which would make brushing more enjoyable for children would provide an inducement lacking in existing toothpaste and dentrifice formulations. A toothpaste which produces a dynamic color change, has a reduced bitter taste and less of the annoying foaming action that often chokes children's small mouths would permit the accomplishment of basic oral hygiene with improved results and less aggravation. In the past, efforts have been made to develop toothpaste formulations which undergo a color change upon brushing. U.S. Pat. No. 4,150,106 discloses a toothpaste containing reagents for controlling the tooth brushing time by the change of color occurring after a predetermined brushing time, the reagents comprising essentially a citrate/citric acid buffer having a specified molarity and pH and chlorophenol red in a specified proportion. U.S. Pat. No. 4,568,534 discloses an alkaline dentrifice incorporating a buffering system which maintains an alkaline pH for a predetermined period of brushing time and at least one color indicator showing color at an alkaline pH and upon contact with saliva causes a color change in the dentrifice within the user's mouth after a predetermined brushing period of time.

There remains a need for an improved toothpaste or dentrifice formulation particularly for use by children which is readily formulated, produces a dynamic color change during brushing independent of the pH in the mouth and which reduces objectionable foaming in the mouth during brushing.

SUMMARY OF THE INVENTION

Among the several objects of the invention may be noted the provision of a novel toothpaste containing color reagents for interacting to provide a color change indicative of tooth brushing time; the provision of such a toothpaste which advantageously produces less foaming to interfere with or diminish the color change; the provision of a toothpaste of this type in which the color change occurs independently of the pH in the mouth; the provision of such a toothpaste which is especially adapted for use by a children to encourage proper oral hygiene; and the provision of such a toothpaste which can be readily formulated from available materials. Other objects and features will be in part apparent and in part painted out hereinafter.

Briefly, the present invention is directed to a toothpaste containing color reagents for interacting to provide a color change upon brushing indicative of tooth brushing time, the color reagents comprising two separate color components selected from the group consisting of FD&C dyes, FD&C lakes and natural food colors, the separate components being adapted to interact after a predetermined brushing time to produce a third color. Other features include the incorporation of no or very low levels of foaming agents in the toothpaste and the optional provision of a partition interposed between two layers containing the separate color reagents or components to avoid migration and premature interacting of said reagents or components.

DESCRIPTION OF THE PREFERRED EMBODIMENTS

In accordance with the present invention, it has now been found that a non-foaming, color-changing toothpaste can be formulated by incorporating color reagents for interacting to provide a color change indicative of tooth brushing time, the reagents comprising two separate color components selected from the group consisting of FD&C dyes, FD&C lakes and natural food colors, the two separate color components being adapted to interact after a predetermined brushing time to produce a third color. By producing a dynamic color change after a predetermined brushing time with less of the annoying foaming which characterizes many available toothpastes, the toothpaste of the present invention advantageously makes basic oral hygiene more appealing, less aggravating and more effective especially for children. Thus, the secondary color produced by a interacting of the color components of the toothpaste of the invention provides a graphic illustration (a) that brushing is being carried out with an adequate amount of effort; (b) that an adequate amount of time (i.e. 20 to 40 seconds) as elapsed for effective brushing to occur, and (c) which renders the tooth brushing and cleansing experience more attractive and delightful for children.

In carrying out the invention, various combinations of separate color components may be used to produce a distinctive secondary color by interaction of the components upon brushing for times on the order of 20 to 40 seconds or longer. Thus, the separate color reagents or components are selected from the group consisting of FD&C dyes or food colors, FD&C lakes and natural food colors. Among the FD&C dyes or food colors which may be employed are FD&C Blue 1, FD&C Yellow 5, FD&C Red 40, FD&C Yellow 6, FD&C Blue 2, FD&C Red 4 and FD&C Green 6. For example, to achieve a secondary color of green, one employs 75 parts of FD&C Yellow 5 dye at a concentration of 100 ppm and 25 parts of FD&C Blue 1 dye at a concentration of 50 ppm with the final concentration of the two components in the toothpaste being approximately 87.5 ppm. To achieve a secondary color of purple, one employs 70 parts FD&C Red 40 dye at a concentration of 125 ppm and 30 parts FD&C Blue 1 dye at a concentration of 50 ppm with the final concentration of the two components in the toothpaste being approximately 102.5 ppm. To achieve a secondary color of orange, one employs 70 parts FD&C Yellow 5 dye at a concentration of 100 ppm and 30 parts FD&C Red 40 dye at a concentration of 125 ppm with the final concentration of the two components in the toothpaste being approximately 107.5 ppm. In each instance, the two primary dyes or food colors interact after a predetermined brushing time to produce a secondary or third color indicative of brushing time and effort. Other combinations of primary dyes or food colors may also be used to produce other secondary colors which serve the same purpose.

Among the FD&C lakes which may be employed in the practice of the invention are FD&C Blue 1 lake at a concentration of 0.1% (such as that identified as Warner-Jenkinson No. 9901—pure dye 11–13%), FD&C Yellow 5 lake at a concentration of 0.2% (such as that identified as Warner-Jenkinson No. 9733—pure dye 14–16%), FD&C Red 40 lake at a concentration of 0.2% (such as that identified as Warner-Jenkinson No. 9313—pure dye 35–42%), FD&C Yellow 6 lake and other FD&C lakes known to those in the art. Using lakes to achieve a secondary color, for example, to achieve the color green, one employs 70 parts FD&C Yellow 5 lake at a concentration of 0.2% and 30 parts FD&C Blue 1 lake at a concentration of 0.1% with the final concentration of the two components in the toothpaste being approximately 0.17%; to achieve the color purple, one employs 60 parts FD&C Red 40 lake at a concentration of 0.2% and 40 parts FD&C Blue 1 lake at a concentration of 0.1% with the final concentration of the two components in the toothpaste being approximately 0.16%; to achieve the color orange, one employs 70 parts FD&C Yellow 5 lake at a concentration of 0.2% and 30 parts FD&C Red 40 lake at a concentration of 0.2% with the final concentration of the two components in the toothpaste being approximately 0.2%. Other combinations of FD&C lakes may also be used to produce other secondary colors in accordance with the present invention. In general, the use of FD&C dyes or food colors is preferred over the use of FD&C lakes since the latter tend to impart a more opaque and duller appearance to the toothpaste and therefore render it less attractive for children.

The color components used in the practice of the invention may also be natural food colors. These include carmine, carotene, annatto, turmeric, curcumin and other natural food colors know to the art.

In general, the amount of color components incorporated into the toothpaste of the invention may range from approximately 0.01% to approximately 10% by weight. For example, the use of 52% FD&C Red 40 and 48% FD&C Blue 1 in the indicated amounts will yield a purple color upon interacting; the use of 40% FD&C Red 40 and 60% FD&C Yellow 5 will yield an orange color upon interacting; and the use of 30% FD&C Blue 1 and 70% FD&C Yellow 5 will yield a green color upon interacting. Similarly, appropriate amounts within the above-stated range of FD&C Red 40 lake, 35–42% pure dye, FD&C Blue 1 lake, 11–13% pure dye, FD&C Yellow 5 lake, 24–28% pure dye, may be used in carrying out the invention.

Optionally, in order to ensure a longer shelf life without one color component migrating into or interacting with the other color component to prematurely produce a third color, the two separate color components may be maintained in a separate condition by interposing a partition between the color components to effectively separate the color components until the toothpaste of the invention is dispensed onto a toothbrush and subjected to a mixing action in brushing. The partition may be a physical partition in the tube or dispenser interposed between two separate layers of toothpaste each containing one of the two separate color components. The partition may also be constituted by a white paste containing titanium dioxide interposed between the two color components of the toothpaste composition of the invention. Further, the partition may be in the nature of a chemical partition by employing hydrophobic and hydrophilic components each containing one of the respective two color components. The use of FD&C lake colors, such as those mentioned above, also minimizes any premature migration of color components into each other in the toothpaste tube or dispenser prior to brushing.

In general, it is preferred that the toothpaste of the invention contain no foaming agent since any significant amount of such an agent tends to diminish the visibility of the color change occurring upon interaction of the two color reagents or components and thereby render the color change less evident or perceptible. If a foaming agent incorporated in the toothpaste of the invention, no more than approximately 0.05% by weight should be present in order to minimize the disadvantageous effect imparted by foaming agents. Various conventional foaming agents may be used such as sodium lauryl sulfate, sodium N-lauroyl sarcosinate or cocomonoglyceride sulfonate may be used in the practice of the invention with the use of sodium lauryl sulfate being preferred.

The toothpaste of the invention may also contain other conventional ingredients or components such as gelling agents or binders, polishing agents, vehicles, humectants, flavoring agents, sweeteners, and a fluoride containing compound. Thus, from approximately 0.5 to approximately 18% by weight of a gelling agent or binder may be used, the gelling agent being selected from known gelling agents such as sodium carboxymethyl cellulose, xanthan gum, polyvinyl pyrrolidone, hydroxyethyl cellulose, polyvinyl alcohol, Irish moss extract, sodium alginate and mixtures thereof. From approximately 15% to approximately 90% by weight of a polishing agent such as silica gel, silica, sodium aluminum silicate, hydrated alumina, dicalcium phosphate, calcium pyrophosphate, calcium carbonate and mixtures thereof may be incorporated into the toothpaste of the invention. From approximately 10% to approximately 80% by weight of a humectant such as sorbitol, maltitol, polyethylene glycol, glycerin and mixtures thereof may be utilized in the practice of the invention. It is highly preferred that the toothpaste of the invention contain between approximately 0.1 and approximately 2% by weight of a fluoride with sodium fluoride or stannous fluoride being especially preferred. The flavoring agents and sweeteners known to those in the toothpaste art may constitute from approximately 0.1 to approximately 10% by weight of the toothpaste, and water constitutes the most common toothpaste vehicle.

In an optional embodiment of the invention, the toothpaste may contain a flavoring agent or component constituted by encapsulated or agglomerated flavoring crystals, ingredients or components known to those in the art and which upon mechanical agitation bring about a time release (5 to 20 second delayed) flavoring of the toothpaste. The incorporation of such a time released flavor burst in conjunction with the color changing properties of the toothpaste of the invention advantageously induces children to brush for an increased amount of time while encouraging them to utilize enough mechanical scrubbing force to properly brush their teeth.

As used herein, the term "toothpaste" is intended to encompass formulations of both the paste and gel form, the two forms being generally identical except that the paste form contains titanium dioxide. The components or ingredients discussed and enumerated above may be used in both the paste and gel forms of the present invention and, as previously indicated, a white paste containing titanium dioxide may be used as a partition interposed between separate layers of toothpaste containing the respective color components.

The following examples illustrate the practice of the invention.

EXAMPLE 1

A non-foaming tooth gel of the type disclosed in U.S. Pat. No. 5,009,881, dated Apr. 23, 1991, was used. To this gel was added 75 parts by weight of FD&C Yellow 5 dye in liquid form at a concentration of 100 ppm and 25 parts by weight of FD&C Blue 1 dye in liquid form at a concentration of 50 ppm to produce a final concentration of the color components in the gel of 87.5 ppm upon homogeneous mixing of the color components into the gel. The gel produced had an acceptable shelf life stability.

Upon brushing with the resulting gel for approximately 20–40 seconds, a distinctive green color was observed by the interaction of the two color components.

EXAMPLE 2

Example 1 was repeated except that added to the gel were 70 parts by weight of FD&C Red 40 dye in liquid form at a concentration of 125 ppm and 30 parts by weight of FD&C Blue 1 dye in liquid form at a concentration of 50 ppm to produce a final concentration of the color components in the gel of 102.5 ppm upon homogeneous mixing of the color components into the gel. The gel displayed an acceptable shelf life stability.

Upon brushing with the resulting gel for approximately 20–40 seconds, a distinctive purple color was observed by the interaction of the two color components.

EXAMPLE 3

Example 1 was repeated except that added to the gel were 70 parts by weight of FD&C Yellow 5 dye in liquid form at a concentration of 100 ppm and 30 parts by weight of FD&C Red 40 dye in liquid form at a concentration of 125 ppm to produce a final concentration of the color components in the gel of 107.5 ppm upon homogeneous mixing of the color components into the gel. The gel displayed an acceptable shelf life stability.

Upon brushing with the resulting gel for approximately 20–40 seconds, a distinctive orange color was observed by the interaction of the two color components.

EXAMPLE 4

Example 1 was repeated except that added to the gel were 70 parts by weight of FD&C Yellow 5 lake (pure dye 14–16%) dispersed in glycerine at a concentration of 0.2% and 30 parts by weight of FD&C Blue 1 lake (pure dye 11–13%) dispersed in glycerine at a concentration of 0.1% to produce a final concentration of the lake color components in the gel of 0.17% upon homogeneous mixing of the color components into the gel. The gel displayed acceptable shelf life stability.

Upon brushing with the resulting gel for approximately 20–40 seconds, a distinctive green color was observed by interaction of the two lake color components.

EXAMPLE 5

Example 1 was repeated except that added to the gel were 60 parts by weight of FD&C Red 40 lake (pure dye 35–42%) dispersed in glycerine at a concentration of 0.2% and 40 parts by weight of FD&C Blue 1 lake (pure dye 11–13%) dispersed in glycerine at a concentration of 0.1% to produce a final concentration of the lake color components in the gel of 0.16% upon homogeneous mixing of the color components into the gel. The gel displayed acceptable shelf life stability.

Upon brushing with the resulting gel for approximately 20–40 seconds, a distinctive purple color was observed by the interaction of the two lake color components.

EXAMPLE 6

Example 1 was repeated except that added to the gel were 70 parts by weight of FD&C Yellow 5 lake (pure dye 14–16%) dispersed in glycerine at a concentration of 0.2% and 30 parts by weight of FD&C Red 40 lake (pure dye 35–42%) dispersed in glycerine at a concentration of 0.2% to produce a final concentration of the lake color components in the gel of 0.2% upon homogeneous mixing of the color components into the gel. The gel displayed acceptable shelf life stability.

Upon brushing with the resulting gel for approximately 20–40 seconds, a distinctive orange color was observed by the interaction of the two lake color components.

In view of the above, it will be seen that the several objects of the invention are achieved and other advantageous results attained.

As various changes could be made in the above products, without departing from the scope of the invention, it is intended that all matter contained in the above description shall be interpreted as illustrative and not in a limiting sense.

What is claimed is:

1. A toothpaste consisting essentially of color reagents for interacting to provide a color change indicative of tooth brushing time, said reagents consisting essentially of two separate color components selected from the group consisting of FD&C dyes, FD&C lakes and natural food colors, said two separate color components being selected to interact after a predetermined brushing time of about 20 to 40 seconds to produce a third color, with the proviso that said toothpaste contain no pH responsive color indicator or foaming agent.

2. A toothpaste according to claim 1 wherein from approximately 0.01% to approximately 10% by weight of said color components is incorporated therein.

3. A toothpaste according to claim 1 wherein one of said color components is FD&C Yellow 5, the other of said color components is FD&C Blue 1 and said third color is green.

4. A toothpaste according to claim 1 wherein one of said color components is FD&C Red 40, the other of said color components is FD&C Blue 1 and said third color is purple.

5. A toothpaste according to claim 1 wherein one of said color components is FD&C Yellow 5, the other of said color components is FD&C Red 40 and said third color is orange.

6. A toothpaste according to claim 1 wherein one of said color components is FD&C Yellow 5 lake, the other of said color components is FD&C Blue 1 lake and said third color is green.

7. A toothpaste according to claim 1 wherein one of said color components is FD&C Red 40 lake, the other of said color components is FD&C Blue 1 lake and the third color is purple.

8. A toothpaste according to claim 1 wherein one of said color components is FD&C Yellow 5 lake, the other of said color components is FD&C Red 40 lake and the third color is orange.

9. A toothpaste according to claim 1 wherein a partition is interposed between said two separate color components to prevent migration of one of said color components into the other of said color components.

10. A toothpaste according to claim 9 wherein said partition is constituted by a white paste containing titanium dioxide.

11. A toothpaste according to claim 9 wherein said partition is constituted by a physical partition between said two separate color components.

12. A toothpaste according to claim 1 wherein approximately 15 to 90% by weight of a polishing agent is incorporated therein.

13. A toothpaste according to claim 12 wherein said polishing agent is selected from the group consisting of silica gel, silica, sodium aluminum silicate, hydrated alumina, dicalcium phosphate, calcium pyrophosphate, calcium carbonate and mixtures thereof.

14. A toothpaste according to claim 1 wherein from approximately 0.1 to approximately 2% by weight of a fluoride is incorporated therein.

15. A toothpaste according to claim 14 wherein said fluoride is sodium fluoride.

16. A toothpaste according to claim 14 wherein said fluoride is stannous fluoride.

17. A toothpaste according to claim 1 wherein from approximately 0.5 to approximately 18% by weight of a gelling agent is incorporated therein.

18. A toothpaste according to claim 17 wherein said gelling agent is selected from the group consisting of sodium carboxymethyl cellulose, xanthan gum, polyvinyl pyrrolidone, hydroxyethyl cellulose, polyvinyl alcohol, Irish moss extract, sodium alginate and mixtures thereof.

* * * * *